Oct. 3, 1961 W. ZOMBORY ET AL Plant Pat. 2,098
ROSE PLANT
Filed Dec. 5, 1960
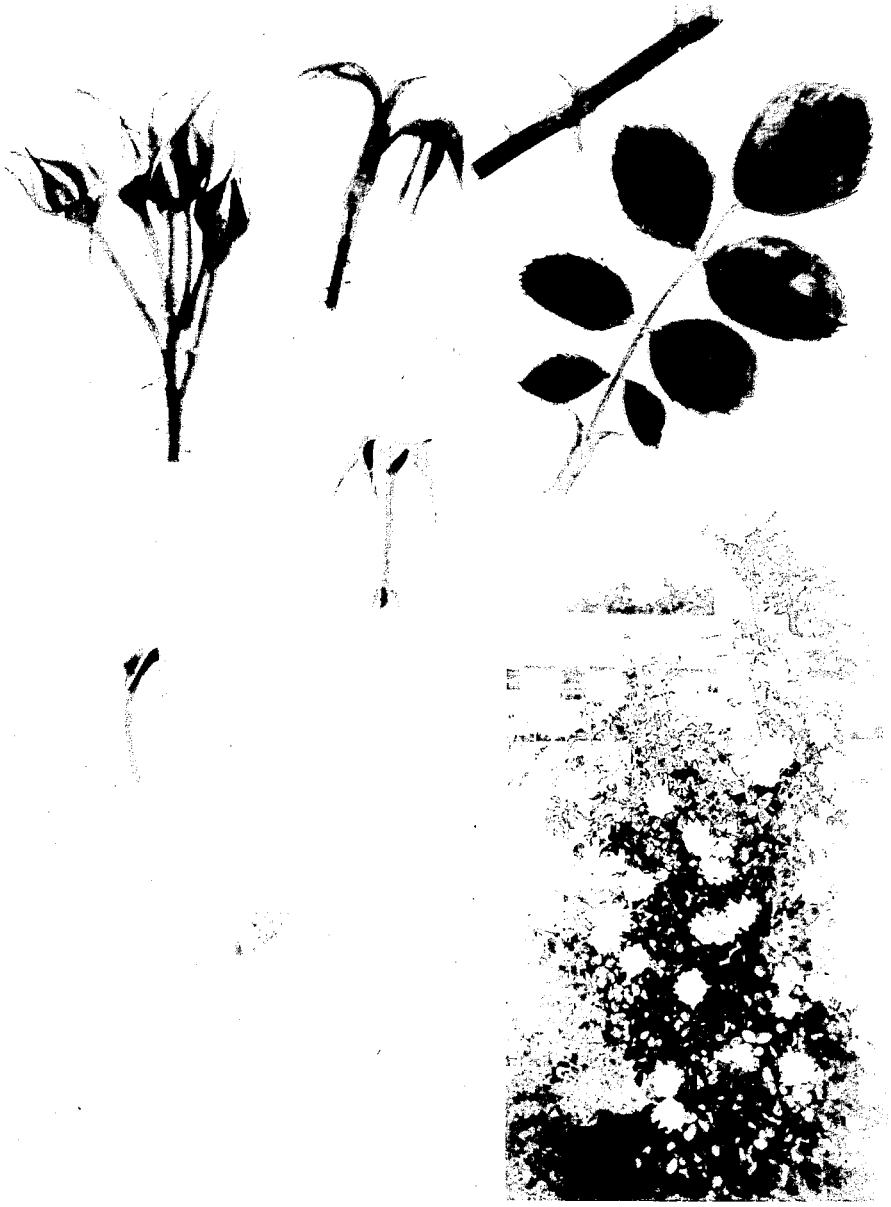
Inventors
William Zombory
Sophia B. Zombory
By: Robb & Robb
Attorneys United States Patent Office Plant Pat. 2,098
Patented Oct. 3, 1961

2,098
ROSE PLANT

William Zombory and Sophia B. Zombory, Detroit, Mich., assignors to Jackson & Perkins Company, Newark, N.Y., a corporation of New York Filed Dec. 5, 1960, Ser. No. 73,942
1 Claim. (Cl. 47—61)

The present invention relates to a new and distinct variety of rose plant of the climber class, which was originated by us by crossing the variety "New Dawn" (Plant Patent No. 1) with the variety "Fashion" (Plant Patent No. 789).

The primary objective of this breeding was to produce a new rose variety of the climber class which bears flowers having a color comparable to that of the flowers of the parent variety "Fashion," combined with the reblooming habit of the parent variety "New Dawn." This objective was fully achieved, along with other desirable improvements, as evidenced by the following unique combination of characteristics which are outstanding in the new variety and which distinguish it from its parents, as well as from all other varieties of which we are aware:

(1) A pillar type habit of growth, with 6 to 8 foot bottom breaks;

(2) A recurrent blooming habit of the new wood throughout the entire growing season;

(3) A free blooming habit; and (4) A distinctive and attractive Eosine Pink general color tonality of the flowers comparable to the color of the flowers of "Fashion."

Asexual reproduction of our new variety by budding, as performed on our behalf at Newark, New York, and also at Pleasanton, California, shows that the aforementioned characteristics and distinctions come true to form and are established and transmitted through succeeding propagations.

The accompanying drawing shows typical specimens of the vegetative growth and flowers of our new variety in different stages of development and as depicted in color as nearly true as it is reasonably possible to make the same in a color illustration of this character, and also shows a complete plant, as depicted in black and white for the purpose of illustrating the climbing habit of growth of the plant.

The following is a detailed description of our new variety, with color terminology in accordance with Ridgway's Color Standards and Nomenclature:

Parentage: Seedling.
*Seed parent.*—"New Dawn."
*Pollen parent.*—"Fashion."

Classification:
*Botanic.*—Climber.
*Commercial.*—Climber.

*Flower*

(Observations made from specimens grown outdoors at Newark, New York, about mid-afternoon during the early part of the month of August.)

Blooming habit: Recurrent—intermittent.

Bud:
*Size.*—Medium.
*Form.*—Ovoid; is not affected by wet or hot weather.
*Color.*—When sepals first divide—Rose Red, Plate 12. When petals begin to unfurl—Geranium Pink. Plate 1. When half-blown: inside of petals—Eosine Pink, Plate 1, with edge of petals lightly overcast with Geranium Pink, Plate 1; reverse of petals—Thulite Pink, Plate 26, lightly overcast with Eosine Pink, Plate 1.

*Sepals.*—Branched; curl back when petals begin to unfurl. Color: inside—Kildare Green, Plate 31; outside—Cress Green, Plate 31.
*Calyx.*—Color—Cress Green, Plate 31. Shape—pear. Size—small. Aspect—smooth. Odor when rubbed—none.
*Peduncle.* — Length — medium. Aspect — smooth. Strength—erect; slender. Color—Lettuce Green, Plate 5.
*Opening.*—Opens up well; is not affected by adverse weather conditions.

Bloom:
*Size.*—Medium. Average size when fully expanded—3½ inches.
*Borne.*—Singly and several together; freely.
*Stems.*—Medium length; strong.
*Form (when first open).*—High-centered. Permanence—retains its form to the end, but outer petals curl back.
*Petalage.*—Double (full but open center). Number of petals under normal conditions—25.
*Color.*—Center of flower—Geranium Pink, Plate 1. Outer petals—Eosine Pink, Plate 1, very lightly overcast with La France Pink, Plate 1. Base of petals (aiglet)—Citron Yellow, Plate 16. Inside of petals—Eosine Pink, Plate 1, lightly overcast with La France Pink, Plate 1 on the outer edges of the petals. Reverse of petals—Thulite Pink, Plate 26. General tonality from a distance—Eosine Pink, Plate 1.
*Discoloration.*—General tonality at end of first day—Eosine Pink, Plate 1. Second day—Eosine Pink, Plate 1, with outer edges of petals lightly overcast with La France Pink, Plate 1. Third day—Eosine Pink, Plate 1, lightly overcast with La France Pink, Plate 1.

Petals:
*Texture.*—Leathery; is not affected by wet or hot weather.
*Appearance.*—Inside—satiny. Outside—shiny.
*Form.*—Oval.
*Arrangement.*—Imbricated (regularly arranged shingle-like).
*Petaloids in center.*—Few; small.
*Persistence.*—Drop off cleanly.
*Fragrance.*—Moderate. Nature—tea (average hybrid tea scent).
*Lasting quality.* — On the plant — long. As cut flower—long.

*Genital organs*

Stamens, anthers: Medium size; many; regularly arranged around styles. Color—Capucine Orange, Plate 3.
Stamens, filaments (threads): Medium length. Color—Light Orange-Yellow, Plate 3.
Pollen: Color—Capucine Buff, Plate 3.
Styles: Bunched; uneven length; short; thin.
Stigmas: Color—Citron Yellow, Plate 16.
Ovaries: All enclosed in calyx.
Hips: None.
Seeds: None.

*Plant*

Form: Climber; pillar-type; from 6 to 8 foot bottom breaks.
Growth: Vigorous; branching.
Foliage: Compound of 3–7 leaflets.
*Size.*—Medium.
*Quantity.*—Abundant.

*Color.*—New foliage: upper side—Yellowish Oil Green, Plate 5, overcast with Oxblood Red, Plate 1; under side—Oxblood Red, Plate 1. Old foliage: upper side—Forest Green, Plate 17; under side—Biscay Green, Plate 17.

*Shape.*—Oval pointed.

*Texture.*—Upper side—leathery; glossy. Under side—smooth.

*Ribs and veins.*—Ordinary

*Edge.*—Serrated (saw-toothed).

*Serration.*—Single; small.

*Leaf stem.*—Color—Biscay Green, Plate 17. Under side—prickly.

*Stipules.*—Medium length; smooth.

Wood:

*New wood.*—Color—Parrot Green, Plate 6. Bark—smooth.

*Old wood.*—Color—Cress Green, Plate 31. Bark—smooth.

Thorns:

*Thorns.*—Quantity: on main stalks from base—many; on laterals from stalk—many. Form—narrow base; short; hooked downward. Color (when young)—Eugenia Red, Plate 13. Position—irregular.

*Prickles.*—Quantity: on main stalks—none; on laterals—none.

*Short needles.*—Quantity: on main stalks—none; on laterals—none.

We claim:

A new and distinct variety of rose plant of the climber class, substantially as herein shown and described, characterized particularly as to novelty by the unique combination of a pillar type of growth, a recurrent blooming habit on the new wood throughout the entire growing season, a free blooming habit, and a distinctive Eosine Pink general color tonality of the flowers comparable to that of the variety "Fashion" (Plant Patent No. 789).

No references cited.